US008119362B2

(12) United States Patent
Barhanin et al.

(10) Patent No.: US 8,119,362 B2
(45) Date of Patent: Feb. 21, 2012

(54) METHOD OF SCREENING FOR COMPOUNDS THAT CAN BE USED FOR THE TREATMENT OF RESPIRATORY CONDITIONS

(75) Inventors: Jacques Barhanin, Nice (FR); Christian Gestreau, Marseilles (FR); Richard Warth, Regensburg (DE); Dirk Heitzmann, Regensburg (DE); Jörg Thomas, Neu Ulm (DE)

(73) Assignees: Centre National de la Recherche Scientifique—Cnrs, Paris Cedex (FR); Universite Paul Cezanne Marseille III, Aix-en-Provence (FR)

( * ) Notice: Subject to any disclaimer, the term of this patent is extended or adjusted under 35 U.S.C. 154(b) by 0 days.

(21) Appl. No.: 12/681,452

(22) PCT Filed: Oct. 3, 2008

(86) PCT No.: PCT/FR2008/001391
§ 371 (c)(1),
(2), (4) Date: May 25, 2010

(87) PCT Pub. No.: WO2009/080910
PCT Pub. Date: Jul. 2, 2009

(65) Prior Publication Data
US 2011/0014642 A1     Jan. 20, 2011

(30) Foreign Application Priority Data
Oct. 5, 2007  (FR) ...................................... 07 06999

(51) Int. Cl.
*C12Q 1/02*  (2006.01)
*C12P 21/06* (2006.01)
*C07K 1/00*  (2006.01)

(52) U.S. Cl. ........................... 435/29; 435/69.1; 530/350
(58) Field of Classification Search .................... 435/29, 435/69.1; 530/350
See application file for complete search history.

(56) References Cited

FOREIGN PATENT DOCUMENTS
WO    WO 2005/054867 A2    6/2005

OTHER PUBLICATIONS

Weir S.W. and Weston A.H., The effects of BRL 34915 and nicorandil on electrical and mechanical activity and on 86Rb efflux in rat blood vessels, Br. J. Pharmac. (1986), 88, 121-128.*
Maria I. Niemeyer et al., Modulation of the Two-pore Domain Acid-sensitive $K^+$ Channel TASK-2 (KCNK5) by Changes in Cell Volume, The Journal of Biological Chemistry, Nov. 16, 2001, pp. 43166-43174, vol. 276, No. 46, The American Society for Biochemistry and Molecular Biology, Inc.
Anja Gabriel et al., Localization of the tandem pore domain $K^+$ channel KCNK5 (TASK-2) in the rat central nervous system, Molecular Brian Research, Jan. 31, 2002, pp. 153-163, vol. 98, No. 1-2, Brain Research Interactive.

* cited by examiner

*Primary Examiner* — Karen Carlson
*Assistant Examiner* — Natalie Moss
(74) *Attorney, Agent, or Firm* — Arent Fox LLP (57) ABSTRACT

The present invention relates to the use of a screening method for identifying candidate molecules that can be used for the treatment of respiratory conditions in a mammal, wherein the screening method comprises a step which comprises determining whether the functional activity of a TASK-2 polypeptide in the presence of a test molecule is decreased or eliminated compared with the functional activity of the TASK-2 polypeptide in the absence of the test molecule, the test molecule being considered to be a candidate molecule when it decreases or eliminates the functional activity.

6 Claims, 8 Drawing Sheets

METHOD OF SCREENING FOR COMPOUNDS THAT CAN BE USED FOR THE TREATMENT OF RESPIRATORY CONDITIONS

CROSS-REFERENCED TO RELATED APPLICATION

This application is a National Stage entry of International Application No. PCT/FR2008/001391, filed Oct. 3, 2008, which claims priority to French Patent Application No. 07/06999, filed Oct. 5, 2007, the disclosure of the prior application is incorporated in its entirety by reference.

SEQUENCE LISTING

The instant application contains a Sequence Listing which has been submitted via EFS-Web and is hereby incorporated by reference in its entirety. Said ASCII copy, created on Jul. 29, 2010, is named 21305312.txt and is 1,872 bytes in size.

TECHNICAL DOMAIN OF THE INVENTION

The present invention relates to the use of a screening method for compounds that can be used for the treatment of respiratory conditions in a mammal. In particular, it may be used to identify new candidate molecules that can be used in the treatment of respiratory conditions.

In the following description, the references in brackets (Ref) refer to the list of references presented after the examples.

PRIOR ART

The central adaptation of respiration to physiological needs is a chemosensitive phenomenon involving changes in the electrical activity of specialised neurons mainly located in the brain stem. These respiratory neurons are distributed in small groups forming columns in the brain stem that extend from the ventrolateral part of the caudal spinal bulb to the dorsolateral part of the pons (Richter D W, Spyer K M (2001) <<Studying rhythmogenesis of breathing: comparison of in vivo and in vitro models>>. *Trends Neurosci*, 24, 464-472 (Ref 1) and Feldman J L, Del Negro (2006) <<Looking for inspiration: new perspectives on respiratory rhythm>>. *Nat Rev Neurosci*, 7, 232-242. (Ref 2)). For this reason, it isn't surprising that ion channel deficiencies are involved in respiratory physiopathologies, for example a long stay in altitude, or different diseases such as the sleep apnoea syndrome and the sudden infant death syndrome.

In mammals, the respiration is controlled by three chemical parameters in the arterial blood:
i) the increase in carbon dioxide, or hypercapnia,
ii) the decrease in the blood pH, or acidosis,
iii) the decrease in the oxygen concentration in the blood, or hypoxia.

The activity of the neuron network controlling respiration is therefore adapted to the different aforementioned parameters (Feldman J L et al. (2003)<<Breathing: rhythmicity, plasticity, chemosensivity>>: *Annu Rev Neurosci*, 26, 239-266 (Ref 3)).

Variations in these parameters are measured with these chemoreceptors. These chemoreceptors detect variations in the pH and partial pressure in arterial $CO_2$ at the peripheral level by means of the chemoreceptors in the carotid body, and in the brain stem by means of the central chemoreceptors located in the raphe nuclei and retrotrapezoid nucleus (Severson et al. (2003)<<Midbrainserotonergic neurons are central pH chemoreceptors>>. *Nat Neurosci*, 6, 1139-1140. (Ref 4)). The electrical signals of the chemoreceptors participate in the adaptation of the respiratory activity to the physiological needs of the organism.

Among the disorders involving deficiencies in the regulation of respiration, the sleep apnoea syndrome is a real public health issue. This syndrome is often associated with obesity. For example, in the United States, about 3 million men and 1.5 million women suffer from the sleep apnoea syndrome. This syndrome may have negative effects on the health of those suffering from it, for example by aggravating cardiovascular diseases as indicated in the article by Namen et al. ((2002) <<Increase in Physician-reported sleep apnea: the National Ambulatory Medical Care Survey>>. Chest 121(6): 1741-1747 (Ref 5)).

The different forms of sleep apnoea involve pathological pauses in respiration during sleep (over 10 seconds in the adult, or more than 8 seconds in the child), inducing hypoxia with a reduced supply of oxygen to the brain and peripheral tissue. The aetiology of sleep apnoea syndromes is heterogenous and may be classified according to the probable underlying disorders. For example, the sub-group of obstructive sleep apnoea is characterised by an obstruction in the upper respiratory tract that prevents proper and effective ventilation. The sub-group of central sleep apnoea is characterised by failures in the regulation of respiration in the brain stem, the nervous control of the respiratory muscles only functioning in a transient manner. The sub-group of mixed apnoea corresponds to a central apnoea followed by an obstructive apnoea.

It is interesting to note that one of the central forms of apnoea (<<non hypercapnic central sleep apnoea>>) is characterised by periods of hyperventilation that result in a reduction in the concentration of arterial carbon dioxide called hypocapnia. The reduction in carbon dioxide in turn induces a failure in the stimulation of the respiratory centres of the brain stem which results in longer pauses in respiration and, as a result, provokes a reduction in the concentration of arterial oxygen.

Apparently, patients suffering from these forms of sleep apnoea have a delay in the stimulation of respiration induced by hypoxia.

Several factors leading to the reduced stimulation in respiration may aggravate sleep apnoea syndromes: for example, substances with an effect on respiration, such as alcohol and tranquillisers, or a stay at high altitude.

Currently, the treatment of sleep apnoea syndromes involves surgical procedures and devices to establish a positive pressure in the upper respiratory tract.

Treatment by assisted breathing consisting of nasal continuous positive airway pressure (nCPAP) during sleep is currently the most effective way to improve the clinical symptoms. However, this treatment requires the patient to be permanently connected to the system by means of a mask. Therefore, the fact that the technique is not very practical limits its therapeutic success.

In addition to surgery and nCPAP treatment, several pharmaceutical approaches have been tried in order to improve the respiration in patients suffering from sleep apnoea, for example by using progesterone, theophylline, acetazolamide and protriptylin.

Even if these substances are able to stimulate the respiration, at least in some patients, none of them has been found to be really effective in the treatment of sleep apnoea syndromes. Besides, some of these substances present major adverse effects. Therefore, a great many pharmaceutical industries are looking for new molecules to treat sleep apnoea syndromes.

In the past, researchers have been interested in the development of TASK-1 potassium channel inhibitors that seem to stimulate the respiration. The TASK-1 channels belong to the family comprising the TASK 1, TASK 2 and TASK 3 channels. They are K+ channels with 4 transmembraine domains and two channel domains (K2P channel) (Goldstein S A et al. (2005), <<International Union Pharmacology. LV. Nomemclature and molecular relationship of two-P potassium channels>>. *Pharmacol Rev,* 57, 527-540. (Ref 6)). These channels are active in the form of monomers, heterodimers and homodimers (Czirjak G, Enyedi P (2001), <<Formation of functional heterodimers between the TASK-1 and TASK-3 two pore domain potassium channel subunits>>. *J. Biol Chem,* 277, 5426-5432. (Ref 7), see Kang D et al. (2004), <<Functionnal expression of TASK-1/TASK-3 heteromers in cerebral granule cells>>. *J. Physiol,* 554, 64-77 (Ref 8) and Berg A P et al. (2004), <<Motoneurons express heteromeric TWIK-related acid sensitive K+(TASK) channels containing TASK-1 (KNCK3) and TASK-3 (KNCK9) subunits>>. *J. Neurosci,* 24, 6693-6702 (Ref 9)). These channels produce a K+ current inhibited by external acidification and after the activation of receptors coupled with G proteins (Mathie A (2007) <<Neuronal two pore domain potassium channels and their regulation by G protein coupled receptors>>. *J. Physiol,* 578, 377-385 (Ref 10)). They are activated by volatile anaesthetics (for example halothane, isoflurane) (see Patel A J, Honore E (2001) <<Properties and modulation of mammalian 2P domain K+ channels>>. *Trends Neurosci,* 24, 339-346 (Ref 11).

The TASK-1 channels are abundant in the brain, the adrenal glands, the blood vessels and the heart. Based on the observations carried out in the <<knock-out>> mouse for TASK-1, the genetic inactivation of TASK-1 was found to lead to aldosterone secretion disorders, arterial hypertension and electrocardiogram changes. In addition, pulmonary hypertension may also be observed. For these different reasons, the use of TASK-1 inhibitors does not seem to be an acceptable solution for a therapeutic treatment.

Recently, central chemosensitivity in response to hypercapnia has been shown to persist in double mutant TASK1/TASK3 mice while the chemosensitivity of the raphe nuclei is eliminated (Mulkey et al. (2007) <<TASK channel determine pH sensitivity in select respiratory neurons but do not contribute to central respiratory chemosensitivity>>. *J. Neurosci,* 27, 14049-14058. (Ref 12)).

The term <<sudden infant death syndrome>> is used for unexplained cases of the death of young children and is the main cause of mortality in children under the age of one year. In most cases, the cause of death is not clearly identified, but respiration disorders seem to play a major role. For children at risk, a system of respiratory monitoring is available, although a pharmaceutical treatment still does not exist.

At high altitude, hypoxia leads to an increase in the ventilation that, in turn, induces a reduction in arterial carbon dioxide (hypocapnia) and, as a result, an increase in the arterial pH (respiratory alkalosis). Respiratory alkalosis affects the regulation of the respiration and leads to irregular modes of respiration, in particular during the phases of sleep. Substances able to inhibit respiratory alkalosis, for example acetazolamide, have been shown to improve the respiratory modes and the associated symptoms at high altitude by increasing the elimination of bicarbonate by the kidneys, thereby resulting in a reduction in the arterial pH. Nevertheless, the use of acetazolamide may induce adverse effects by, for example, perturbing the electrolytic homeostasis.

In short, few substances are currently known to treat these respiratory conditions, and those that are known are insufficiently effective, or present negative adverse effects that limit their use in long-term treatments. In addition, researchers do not have the means to demonstrate new candidate substances for the treatment of respiratory conditions.

There is therefore a real need for new means that can be used to identify new candidate molecules for the treatment of respiratory conditions.

DESCRIPTION OF THE INVENTION

The present invention specifically responds to the aforementioned need by providing a screening method that can be used to identify candidate molecules for the treatment of respiratory conditions in a mammal, said screening method comprising a step consisting of determining whether the functional activity of a TASK-2 polypeptide (KCNK5) in the presence of a test molecule is reduced or eliminated compared with the functional activity of said TASK-2 polypeptide without said test molecule.

If the activity of TASK-2 is found to decrease or is eliminated during the application of the procedure in the invention, the test molecule is considered to be a candidate molecule for the treatment of respiratory conditions in a mammal.

The inventors of the present invention are actually the first to have demonstrated that the TASK-2 channels, also called KCNK5, are present in certain regions of the respiratory centres of the brain stem and surprisingly play a role in respiration. In vitro experiments on a brain stem preparation obtained from newborn mice, present a high reduction in respiratory activity during anoxia. This reduction is no longer observed on brain stem preparations obtained from mice invalidated for the TASK-2 channel. The inhibition or absence of TASK-2 therefore protects against anoxia. This data indicates that the expression of these channels in certain neurons is directly or indirectly associated with the chemoreception.

The inventors of the present invention have also demonstrated the expression of these TASK-2 channels in certain neurons known to be directly or indirectly associated with the chemoreception.

The inventors have also demonstrated that mutant mice invalidated for the inactive TASK-2 channel (TASK-2 knock-out mice) present a remarkable maintenance of respiration during hypoxia, contrary to wild type mice that present a strong respiratory depression. These results demonstrate that in the mouse, in vivo, the inactivation of the TASK-2 channels deeply modifies the ventilatory response during hypoxia and results in a stimulation of respiration.

It is interesting to note that an in vitro system of cell culture was used to demonstrate that the expression of TASK-2 is reduced after several hours of hypoxia due to the sensitivity to hypoxia of the TASK-2 promoter (Brazier et al. (2005) <<Cloning of the human TASK-2 (KCNK5) promoter and its regulation by chronic hypoxia>>. *Biochem Biophys Res Commun* 336:1251-1258 (Ref 13)).

Thereby, the adaptation to hypoxia (for example, during a stay at high altitude), may include a defense mechanism of the body by reduction of the expression of TASK-2 channels. However, this physiological adaptation probably requires several hours and does not function for an immediate response to short-term hypoxia.

In these cases of short-term hypoxia, the pharmacological inactivation of TASK-2 may help anticipate the defense mechanisms of negative regulation of the expression of TASK-2.

In addition, as opposed to the TASK-1 and TASK-3 channels, which are also probably involved in the regulation of respiration due to their expression in multiple groups of chemosensitive respiratory neurons (Sirois et al. (2000) <<The TASK-1 two-pore domain K+ channel is a molecular substrate for neuronal effects of inhalation anesthetic>>. *J. Neurosci,* 20, 6347-6354 (Ref 14)), the expression of TASK-2 in the central nervous system is extremely low and limited to restricted groups of neurons from the respiration circuits (Reyes R et al. (1998) <<Cloning and expression of a novel pH-sensitive two pore domain K+ channel from human kidney>>. *J. Biol Chem,* 273, 30863-30869 (Ref 15)). In addition, TASK-2 is not or is very weakly expressed in the heart where TASK-1 is very strongly expressed. Therefore, the very limited expression of TASK-2 in the central nervous system and its virtual absence in the heart is a huge advantage for the specific inhibition of TASK-2.

The TASK-2 peptide sequence, its organisation in the cell membranes and the coding gene are described in WO00/27871 (PCT/1299/01886—belonging to the CNRS, registered on 9 Nov. 1999 and published on May 2000). This document also describes the cell distribution of TASK-2 in man and in the mouse, the distribution of TASK-2 RNAm in the adult kidney, the chromosome map of TASK-2, the expression of TASK-2 in transfected COS cells and in Xenopus ovocytes, the sensitivity of TASK-2 currents to the pH, as well as the regulation of TASK-2 according to the pH, as well as the biophysical and pharmacological properties of TASK-2. These elements may be used in the present in order to understand and apply the present invention.

<<Respiratory conditions>> refers to respiratory impairment due to a dysfunction in the central nervous system, in particular any respiratory impairment related to a failure in the functioning of the cerebral respiratory centres located in the brain stem.

Among the respiratory conditions, we can note, without limiting ourselves: the sleep apnoea syndrome, the respiratory forms of the sudden infant death syndrome, the models of pathological respiration due to altitude, Ondine's curse or congenital central hypoventilation syndrome, disorders due to accidental or voluntary intoxication by a drug (for example by the absorption of barbiturates or morphinics), respiratory depression related to a general anaesthetic, acute respiratory failure and severe hypoxemia.

<<Test molecule>> refers to a molecule tested by the method in the invention to determine whether it reduces or eliminates the activity of the TASK-2 channel or its expression.

<<Candidate molecule>> refers to a molecule identified by the application of the present invention as reducing or eliminating the activity of the TASK-2 channel or its expression.

The present invention can identify candidate molecules for the treatment of respiratory conditions in a mammal, whether human or animal.

The test molecules for the application of the present invention may be selected, for example at random in molecule banks or, for example, from among biologically acceptable molecules able to integrate with an ion channel.

As test molecules likely to reduce or eliminate TASK-2 activity, we can, for example, mention quinine, quinidine, clofilium, lidocaine, bupivacaine, doxapram as well as volatile anaesthetics such as halothane.

As candidate molecule, we can, for example, also mention an antibody directed against TASK-2. This antibody may be produced by the techniques familiar to one skilled in the art. This antibody, for example, may be a polyclonal, monoclonal, chimeric antibody or a Fab fragment.

<<Functional activity>> refers to the ability of the potassium channel to conduct and control the ion movements through the cell membrane.

According to the invention, the step to determine the functional activity of TASK-2 may be carried out according to one of the methods familiar to one skilled in the art to determine the activity of an ion channel. By way of example, it may consist of a method as described for the KCNK2 channel in document WO 05/054866 (PCT/EP/2004/012823—Bayer Healthcare AG, registered on 12 Nov. 2004 and published on 16 Jun. 2005), a method such as that described for TASK-2, TWIK-1, TREK-1 and TASK-1 channels in aforementioned document WO 00/27871, or even a method such as that described for the TREK-2 channel described in WO 02/00715 (PCT/IB01/01436—CNRS, registered on 27 Jun. 2001 and published on 3 Jan. 2002).

According to the invention, the step consisting of determining whether the functional activity of the TASK-2 polypeptide is reduced or eliminated may comprise:

i) the contact of a cell expressing a TASK-2 polypeptide presenting a functional activity, with said test molecule, and ii) the measurement of the functional activity of the TASK-2 polypeptide and/or its expression in the presence of said test molecule.

Examples of the application of this step are in particular described in the three aforementioned documents.

According to the invention, the cell expressing the TASK-2 polypeptide may express it in an endogenous manner or in recombinant form. Methods that can be used to have this polypeptide expressed by cells for the application of the present invention are described, for example, in WO 00/27871 (COS cells or Xenopus ovocytes) and in the other aforementioned documents.

In general, according to the invention, the functional activity may be measured by one or several parameters selected in the group comprising: the ion current crossing the TASK-2 polypeptide, the change in the membrane potential of the cell expressing the TASK-2 polypeptide, the change in the intracellular ion concentration of the cell expressing the TASK-2 polypeptide. Examples of the measurement of the functional activity of a channel that can be used in the present invention are provided, for example, in each of the three aforementioned documents.

According to the invention, the functional activity may, for example, be determined by the measurement of the ion current crossing the TASK-2 polypeptide, the ion current crossing the TASK-2 polypeptide may, for example, be an efflux of rubidium ions. Preferably, the ion current crossing the TASK-2 polypeptide is measured by determining the efflux of rubidium ions, this may, for example, be determined by atomic absorption spectroscopy, for example as indicated in Gill et al. (2007) (Gill S et al. (2007<<A cell-based rb(+)-flux assay of the kv1.3 potassium channel >>. Assay Drug Dev Technol 5, 37380 (Ref 16)).

According to the invention, a test molecule that reduces the activity of TASK-2 preferably by at least de 10%, preferably by at least 50%, and even more preferably by 75%, 90% or 100% is identified as a candidate molecule to reduce the activity of TASK-2.

In particular, the invention enables the identification of candidate molecules for the treatment of respiratory conditions chosen in the group comprising the sleep apnoea syndrome, the respiratory forms of the sudden infant death syndrome, the models of pathological respiration due to altitude.

A subsequent step in the identification of a candidate molecule may be a step to study the effect of said molecule on respiratory conditions, for example after the administration of the candidate molecule in an animal model presenting respiration disorders or put in conditions inducing respiratory conditions.

Therefore, another aspect of the invention concerns the use of a molecule modulating the functional activity of the TASK-2 polypeptide and/or inhibiting its expression, for the preparation of a composition for the treatment of respiratory conditions.

According to one variant of the present invention, it is also possible to screen molecules to search for those that are able to increase, reduce or eliminate the genetic expression of TASK-2. For example, it consists of determining, for each molecule tested, the level of TASK-2 coding RNAm or generated TASK-2. This may be determined by any method familiar to one skilled in the art. It may consist of a qualitative or quantitative method. The methods of determination that can be used in the present invention may be found, for example, in documents WO 05/054866, WO 00/27871 and WO 02/00715. The presence of an TASK-2 coding RNAm or TASK-2 may, for example, be determined by one of the immunochemical methods familiar to one skilled in the art, for example by immunoassay, a Western blot technique or by immunohistochemistry.

The screening of the present invention may be carried out in a system with or without cell. Any cell expressing TASK-2 may be used. The TASK-2 polypeptide may naturally be expressed in the cell or may be introduced in the cell by a gene recombination technique familiar to one skilled in the art. Examples of the gene recombination protocols that can be used in the present invention are described in the aforementioned three documents.

Therefore, according to this variant, a candidate molecule may, for example, be a complementary sequence to the polynucleotide sequence coding TASK-2 (or KCNK5) likely to block the channel transcription.

The expression vectors derived from retroviruses, adenoviruses, vaccine or herpes viruses or other bacteria viruses may be used to deliver complementary nucleotide sequences to the target organs, tissues or cell populations. Methods familiar to one skilled in the art may be used in the construction of vectors that express the nucleic acid sequence complementary to the polynucleotides of the genes coding TASK-2 (Scott J K, Smith G P (1990) <<Searching for peptide ligands with an epitope library>>. *Science*, 249:386-390 (Ref 17)). Methods familiar to one skilled in the art may be used to construct expression vectors containing TASK-coding sequences as well as elements controlling the transcription and translation. These methods include in vitro techniques of recombinant RNA, synthetic techniques and in vivo gene recombination. The aforementioned three documents describe methods that can be used to construct vectors for the application of the present invention.

Other advantages will appear when reading the following examples provided by way of illustration in reference to the appended figures.

BRIEF DESCRIPTION OF THE DRAWINGS

FIGS. 5A-5E describe the location of the TASK-2 channels present in the brain stem of an adult mouse. 5A: whole brain, ventral surface of the brain stem around the facial motor nucleus (VII) and enlargement showing the retrotrapeizoid nucleus and the parafacial respiratory group (RTN/pfRG). From 5B to 5E: location of the cells expressing TASK-2 on coronal sections. 5B: mesencephal, dorsal raphe (DR). 5C: rostral pons, lateral nucleus of the superior olive (LSO). 5D: caudal pons, ventral surface (RTN/pfRG) and parvocellular reticular nucleus (PCRtA). 5E: rostral spinal bulb, caudal end of VII. 5F: summary diagram showing the distribution of cells expressing TASK-2 on a sagittal section of the brain stem. Other abbreviations: 3N, oculomotor nucleus; 4V, $4^{th}$ ventricle; 7N, facial nucleus; 10N, dorsal vagal motor nucleus; 12N, Duval's nucleus; Amb, ambiguous nucleus; AP, area postrema; CIC, caudal nucleus of the inferior colliculus; ILL, intermediate nucleus of the lateral lemniscus; IO, inferior olive; me5, mesencephalic tract of the trigeminal nerve; Sol, nucleus of the solitary tract.

In FIG. 7A, the Ordinate represents the current volume (VT), the respiratory frequency (RF) and the breathing airflow per minute (MV) expressed in ml/min/g; the Abscissa represents the different tests used in this example as a function of time. In FIG. 7B, the same parameters are represented on a longer time scale; TE, expiration time. In FIG. 7C, examples of the original lines are represented for individual animals at different times (1, 2, 3 and 4 as indicated in FIG. 7B, last line from the bottom). Immediately after the change in hypoxic atmosphere, the wild type mice and the mutant mice present an increase in respiration (point 2). This response is followed by a depression (point 3) that is only observed in the wild type mice. After 12 hours of hypoxia (point 4) this ventilation is similar in all of the mice.

EXAMPLES

Example 1

Demonstration of the Expression of Task-2 in Brain Stem Neurons

The experiments in this example demonstrate the presence of TASK-2 channels in a major nerve structure belonging to the respiratory centres of the brain stem.

These experiments were carried out with mutant adult heterozygote mice (TASK-2$^{+/-}$). The TASK-2 gene that is invalidated is replaced by a sequence coding for an enzyme, beta-galactosidase, Thanks to this enzyme, the cells that normally express the TASK-2 channels may easily be identified by the classic histochemical detection technique using X-Gal as substrate that turns blue when hydrolysed.

After a fixation protocol with para-formaldehyde, a sample of the nerve tissue is taken and then the X-GAL detection technique is carried out on 30 μm thick transverse sections of the brain stem, obtained with a cryostat. At the end of this reaction, the cells expressing the TASK-2 channels are coloured blue (arrow in FIG. 1).

Figure 1:
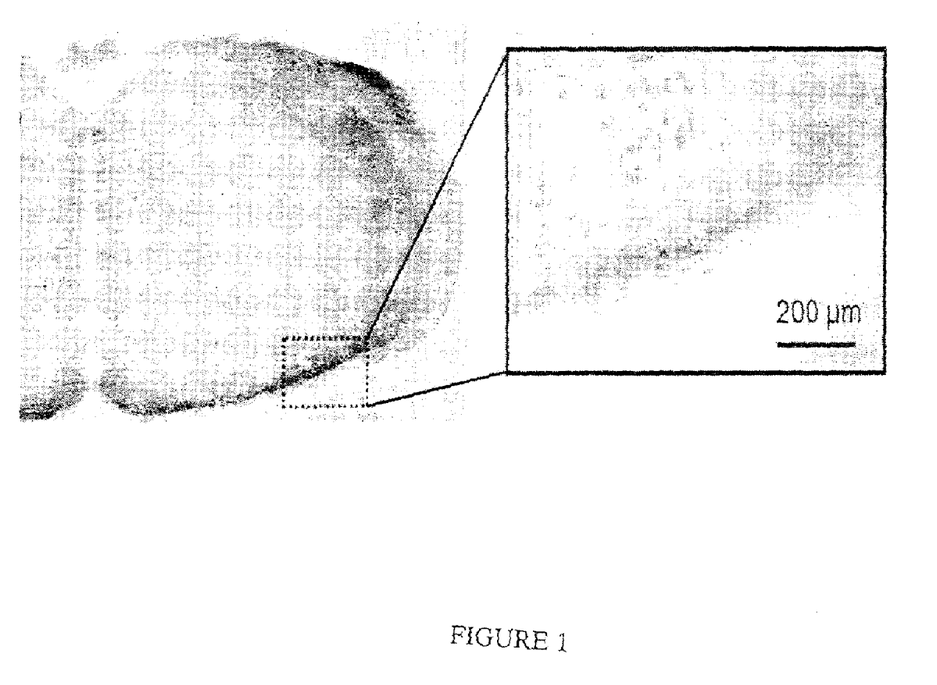
FIG. 1 is a photograph of TASK-2 channels present at the ventral surface of the rostral spinal bulb.

The results obtained reveal the presence of cells expressing TASK-2 in discrete zones of the brain stem. By way of example, FIG. 1 illustrates the TASK-2 channels present at the ventral surface of the rostral spinal bulb. It is a transverse section illustrating the presence of X-gal marking in the neurons of the ventral surface of the rostral spinal blub (retrotrapezoid nucleus, RTN).

As shown in a great many studies, this zone plays a fundamental role in the central chemosensitivity, that is, in the adaptation of the ventilation in response to a chemical variation in the inner medium (blood, cerebrospinal fluid or CSF). Due to the unique location of these channels in the key zones involved in the control of respiration, it is therefore possible to consider specifically modulating the respiration by means of a procedure acting on TASK-2.

Example 2

In Vitro Demonstration of the Intervention of TASK-2 Channels in the Central Mechanisms of the Adaptation of Respiration In this example, the inventors used wild type mice (active TASK-2 channels) and mutant TASK-2 mice that do not express active TASK-2 channels (<<TASK-2$^{-/-}$>>). These mice were initially produced by the W. SKARNES Laboratory in San Francisco in the public domain. They were retrocrossed in the genetic background C57BI/6J then bred and produced within the laboratories of the inventors.

The experiments in this example demonstrate changes in respiratory activity during anoxia. These experiments were carried out on the isolated brain stem preparation in vitro using 1 to 3 day old mice with a "en bloc" preparation.

The brain stem of the wild type or mutant mice (TASK-2$^{-/-}$) is quickly dissected in ice, isolated from the adjacent tissue, then placed in artificial CSF (CSFa) equilibrated in carbogen (95% $O_2$, 5% $CO_2$). The ventral root of spinal segment C4 is at the origin of the phrenic nerve that innervates the diaphragm. This nerve root is taken up inside a glass electrode in order to collect the rhythmic respiratory activity spontaneously generated by the preparation. The electrical activity of root C4 is filtered, amplified, visualised and stored on computer for subsequent analysis of the respiratory parameters (frequency, amplitude, duration). The tests consisted of modifying the quantity of gas dissolved in the CSFa or its chemical composition and comparing the respiratory activities.

Figure 2:
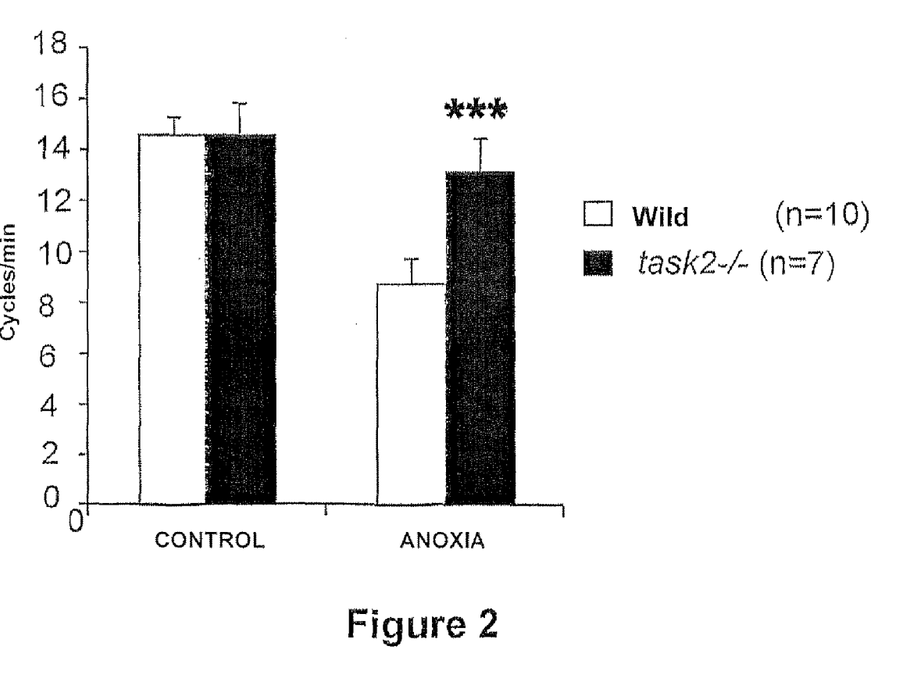
FIG. 2 is a histogram representing the experimental results of example 2 below of the in vitro demonstration of the intervention of the TASK-2 channels in the mechanisms of central chemosensitivity. In this figure, the Ordinate represents the frequency of the respiratory rhythm (expressed in number of cycles per minute), and the Abscissa, the different tests used in this example. The white bars correspond to the results obtained in the wild type mouse and the black bars in the mutant TASK-2 mouse.

FIG. 2 is a histogram representing the experimental results of this example ("en bloc" preparation: respiratory frequency and electrical activity of root C4 of the phrenic nerve recorded in the wild type and TASK-2-/- mouse). Control: artificial CSF equilibrated in 95% $O_2$, 5% $CO_2$. Anoxia: 95% N2, 5% $CO_2$. The Ordinate represents the frequency of the respiratory rhythmic activity (expressed in number of cycles per minute), and the Abscissa, the different tests used in this example. The white bars correspond to the results obtained on the wild type mice and the black bars on the mutant TASK-2 mice.

The results obtained demonstrate that, in control conditions (95% $O_2$, 5% $CO_2$), there is no difference in the respiratory frequency between the wild type animals and the mutant TASK-2 mice. In anoxia (CSFa equilibrated in an oxygen-free gas: 95% $N_2$, 5% $CO_2$), the respiratory frequency of the wild type mice drops by about 40%. This classic response, called hypoxic respiratory depression, is no longer observed in the mutant TASK-2$^{-/-}$ mice (statistical comparison, ***: p<0.001).

These experiments demonstrate that the in vitro respiratory activity of mice subject to anoxia is significantly more frequent after invalidation of the gene coding for the TASK-2 channels. Therefore, in conditions of respiratory depression, it is possible to consider restoring the central respiratory activity by means of a procedure acting on TASK-2.

Example 3

In Vivo Demonstration of the Intervention of Task-2 Channels in the Mechanisms of Respiration In this example, the inventors also used wild type and mutant TASK-2 mice.

The respiration of the mice was measured with a plethysmograph (EMKA technologies, France).

Figure 3:
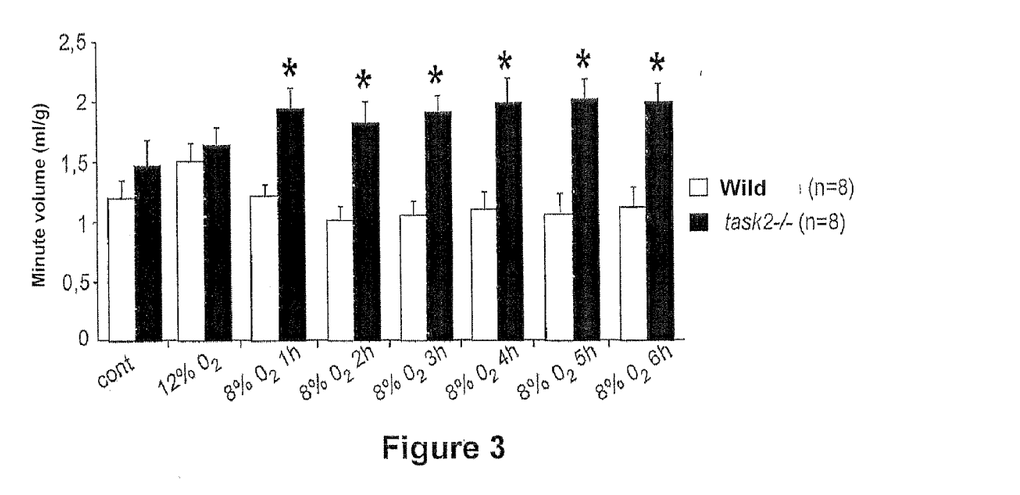
FIG. 3 is a histogram representing the experimental results of example 3 below of the in vivo demonstration of the intervention of TASK-2 channels in the mechanisms of respiration. In this figure, the Ordinate represents the breathing airflow per minute or MV expressed in ml/min/g of body weight, and the Abscissa, the different tests applied in this example.

FIG. 3 is a histogram representing the experimental results of this example illustrating the ventilatory responses of wild type and TASK-2-/- mice with prolonged exposure to hypoxia (8% $O_2$). In this figure, the Ordinate represents the breathing airflow per minute (MV) expressed in ml/min/g, and the Abscissa, the different tests used in this example. The white bars correspond to the results obtained on the wild type mice and the black bars on the mutant TASK-2 mice.

Different conditions of exposure to oxygen were tested, The breathing airflow per minute (ml/min/g) was measured during the control (con) (21% of oxygen) and during a hypoxia at 8% oxygen corresponding to an altitude of 6500 m above sea level. The hypoxia was tested for 1 to 6 hours.

The hypoxia induced a transient increase in respiration in all animals (hyperventilation following the stimulation of peripheral chemoreceptors) (not illustrated). Secondly, the prolonged exposure to hypoxia induced a reduction in the respiratory movements or depression that was only observed in the wild type mouse. The reduction in arterial carbon dioxide following the initial hyperventilation was an important factor in the wild type mouse (in white in the histogram in FIG. 1) in reducing their respiration.

However, the animals invalidated for the TASK-2 channel present sustained ventilation during the entire duration of the hypoxia.

It is clear that after the inactivation of the TASK-2 channels, the hypoxia is a powerful stimulus for respiration, including in conditions of hypocapnia (respiratory alcalosis). It is probable that respiratory alkalosis is no longer able to activate the TASK-2 channels of the central nervous system.

The results of these experiments clearly show that a TASK-2 knock-out mouse presents an increase in respiration during hypoxia when compared with a wild type mouse.

Therefore, the inhibition of TASK-2 seems to be a means of treatment of respiratory conditions.

In conclusion, the inactivation of the TASK-2 potassium channels seems to be a means to stimulate respiration in hypoxic conditions and is a new strategy that differs from the therapeutic approaches used in the prior art.

Example 4

Location of the Expression of Task-2 in the Brain Stem

The mice and the conditions used in this experiment are identical to those in example 1.

The vector used for the generation of TASK-2$^{-/-}$ mice contains a gene coding for beta-galactosidase as described in Mitchell K J et al. (2001) <<Functional analysis of secreted and transmembrane proteins critical to mouse development>>. Nat Genet, 28, 241-249 (Ref 18). The expression of TASK-2 cells was visualised using a TASK-2 promoter directing the activity in the TASK-2-/+ mouse. Surprisingly, a specific marking with X-gal is limited to few regions in the brain stem. No cells expressing TASK-2 were found in other regions of the brain.

The marking found at the spinal bulb is limited to the ventrolateral part of the ventral surface.

The cells expressing TASK-2 form a bilateral column extending over 1.5 mm, from 500-700 μm in front of the obex to the rostral pole of the facial motor nucleus (VII). These cells form clumps located in the marginal zone at the surface of the brain stem and in the tissue parenchyma between 100 to 300 μm deep (see FIG. 5). This region corresponds to the perifacial region grouping the retrotrapezoid nucleus and the parafacial respiratory group (RTN/pfRG).

In the pons, the cells expressing TASK-2 are observed in the lateral part of the superior olive (FIG. 5C), the parvocellular reticular nucleus (FIG. 5D), and the dorsal raphe nuclei and the intermediate lateral lemniscus. Partial marking is detected in the inferior caudal colliculus.

Marking was not detected in the cervical spinal cord corresponding to the phrenic motor nucleus.

As demonstrated in example 1 and in this experiment, TASK-2 channels are present at the ventral surface of the rostral spinal bulb, in particular in the region corresponding to the retrotrapezoid nucleus (RTN) and the parafacial respiratory group (pfRG).

The results obtained demonstrate the presence of cells expressing TASK-2 in discrete zones of the brain stem.

Due to the single location of these channels in the key zones involved in the control of respiration, it is therefore possible to consider specifically modulating the respiration by means of a procedure acting on TASK2.

Example 5

Effect of Hypoxia and Hypercapnia on the Respiration of Mice In Vivo

The mice used in this experiment are identical to those used in example 2 above.

In this experiment, 10 TASK-2$^{+/+}$ mice and 7 TASK-2$^{-/-}$ mice were used.

The central and peripheral chemoreceptors contribute to the adaptation of the respiration by detecting variations in the pH and gases in the blood (Vizek M et al. (1987) <<Biphasic ventilatory response of adult cats to sustained hypoxia has central origin>>. J Appl Physiol, 63, 1658-1664. (Ref 19)). The peripheral chemoreceptor cells located in the carotid bodies more specifically control the rapid increase in the ventilation in response to the hypoxia.

The respiratory adaptation in response to a hypoxia or a hypercapnia of short duration was studied in wild type and mutant mice (TASK-2$^{-/-}$)

The respiration of the mice was measured with a plethysmograph (EMKA technologies, France).

In normal conditions (21% oxygen), the respiratory parameters were identical in the TASK-2$^{-/-}$ and the wild type mouse.

Figure 6:
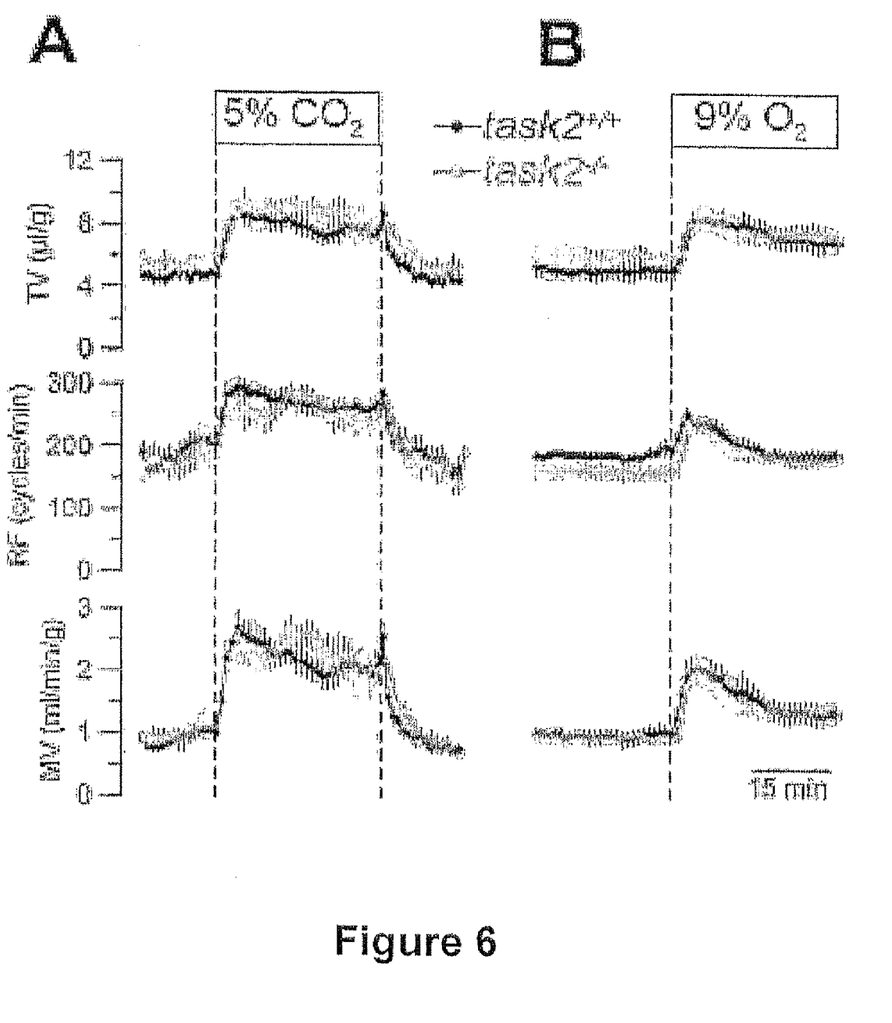
FIGS. 6A and 6B illustrate the respiratory adaptation measured by the plethysmography technique in response to the hypercapnia and the short-term hypoxia in the alert mouse. This adaptation is similar in the wild type mouse or TASK-2 invalidated mouse. In this figure, the Ordinate represents the breathing airflow per minute (MV) expressed in ml/min/g of body weight, the respiratory frequency (RF) and the current volume (VT), the Abscissa, the different tests used in this example as a function of time.

Both types of mice demonstrated a similar increase in respiration in response to an environment comprising 5% CO2 (hypercapnia) (FIG. 6A). A reduction in the oxygen concentration from 21% to 9% also induced an identical increase in the respiration in both types of mice (FIG. 6B).

The hypoxia was transitory and the maximum increase in the respiration appeared after several minutes.

This experiment demonstrates a normal respiratory adaptation in response to a hypoxia of short duration, which is related to the oxygen sensitivity of the peripheral chemosensitive cells located in the carotid bodies. There is also no change in the response to hypercapnia in the mutant mice.

Example 6

Effect of Prolonged Hypoxia on the Transcription of TASK-2

The response to a prolonged hypoxia was also studied. This response was measured at 8% in oxygen over a period of several hours.

The mice used in this experiment are identical to those used in the previous example.

Eight TASK-2$^{+/+}$ and 7 TASK-2$^{-/-}$ mice were used in this experiment.

Figure 7:
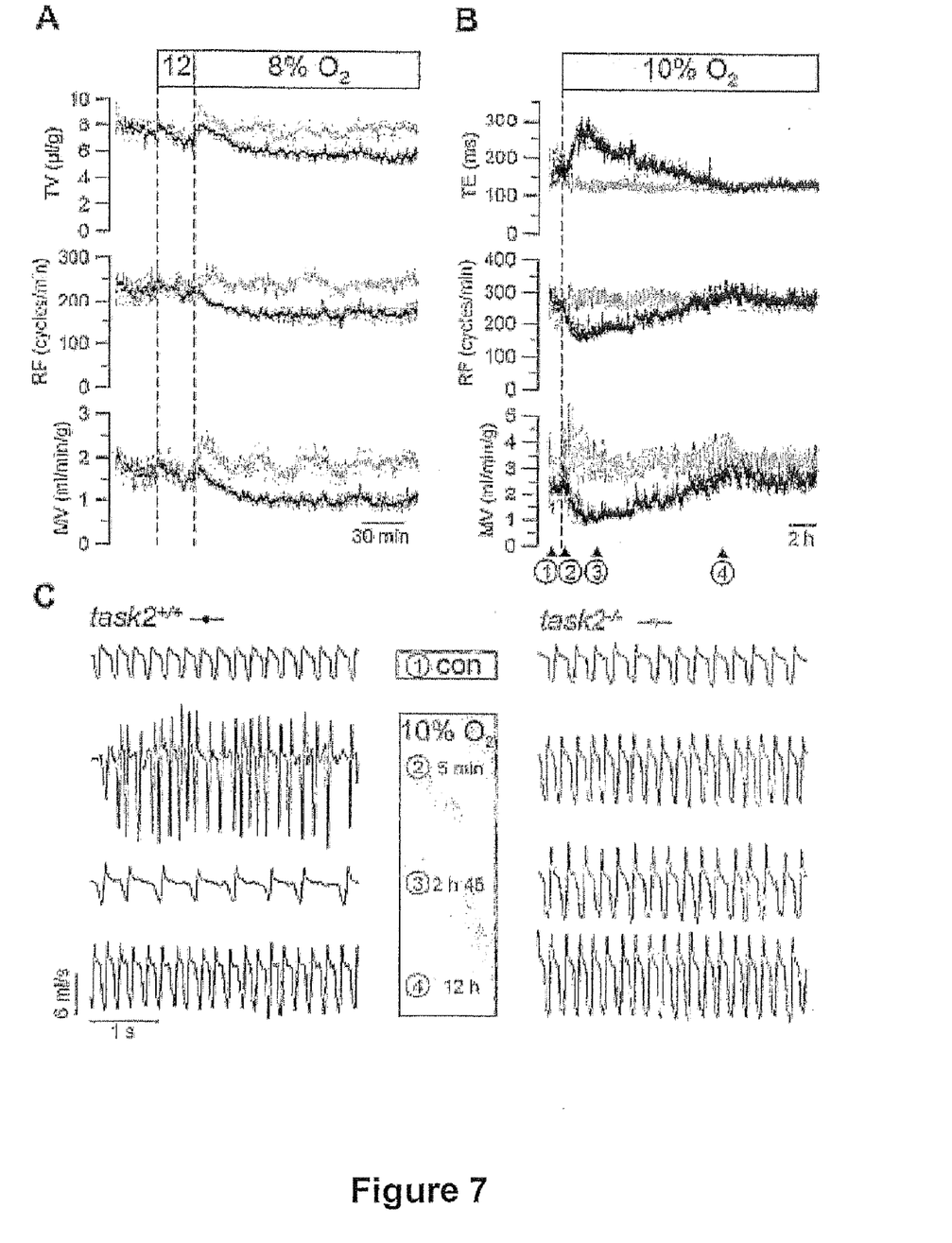
FIGS. 7A 7B and 7C illustrate the respiratory adaptation measured by the plethysmography technique in response to long-term hypoxia. The major respiratory depression observed in the wild type mouse is totally absent in the TASK-2 invalidated mouse.

During a hypoxia of 2 hours, a reduction in the respiration was observed in the control mice (FIG. 7A). A hypoxic depression of the breathing airflow per minute (MV) expressed in ml/min/g, in particular resulted from a reduction in the respiratory frequency (RF). This respiratory depression induced in response to a chronic hypoxia was absent in the TASK-2$^{-/-}$ mouse.

This example shows that the initial response to the hypoxia is normal in the TASK-2$^{-/-}$ mouse. This response corresponds to the stimulation of the peripheral chemoreceptors (Takakura A C et al. (2006) <<Peripheral chemoreceptor inputs to retrotrapezoid nucleus (RTN) CO2-sensitive neurons in rats>>. *J. Appl Physiol*, 63, 1658-1664 (Ref 20)). However, the central respiratory depression induced by the chronic hypoxia is completely absent in the TASK-2$^{--}$ mouse.

Therefore, this experiment clearly indicates that the TASK-2 channel is a critical element for the medullar sensitivity to hypoxia.

As demonstrated in this experiment and in example 2, the inactivation of the TASK-2 potassium channels is therefore a way to inhibit respiratory depression and stimulate respiration in conditions of hypoxia. This inactivation is therefore a new strategy that differs from the therapeutic approaches used in the prior art.

The respiratory adaptation to a chronic hypoxia as described in Powell et al. (Powell F L et al. (1998) <<Time domain of the hypoxic ventilatory response>>. *Respir Physiol*, 112, 123-134. (1998) (Ref 21)) was studied in the following conditions: 10% oxygen corresponding to an altitude of 5300 m for 20 hours.

Figure 8:
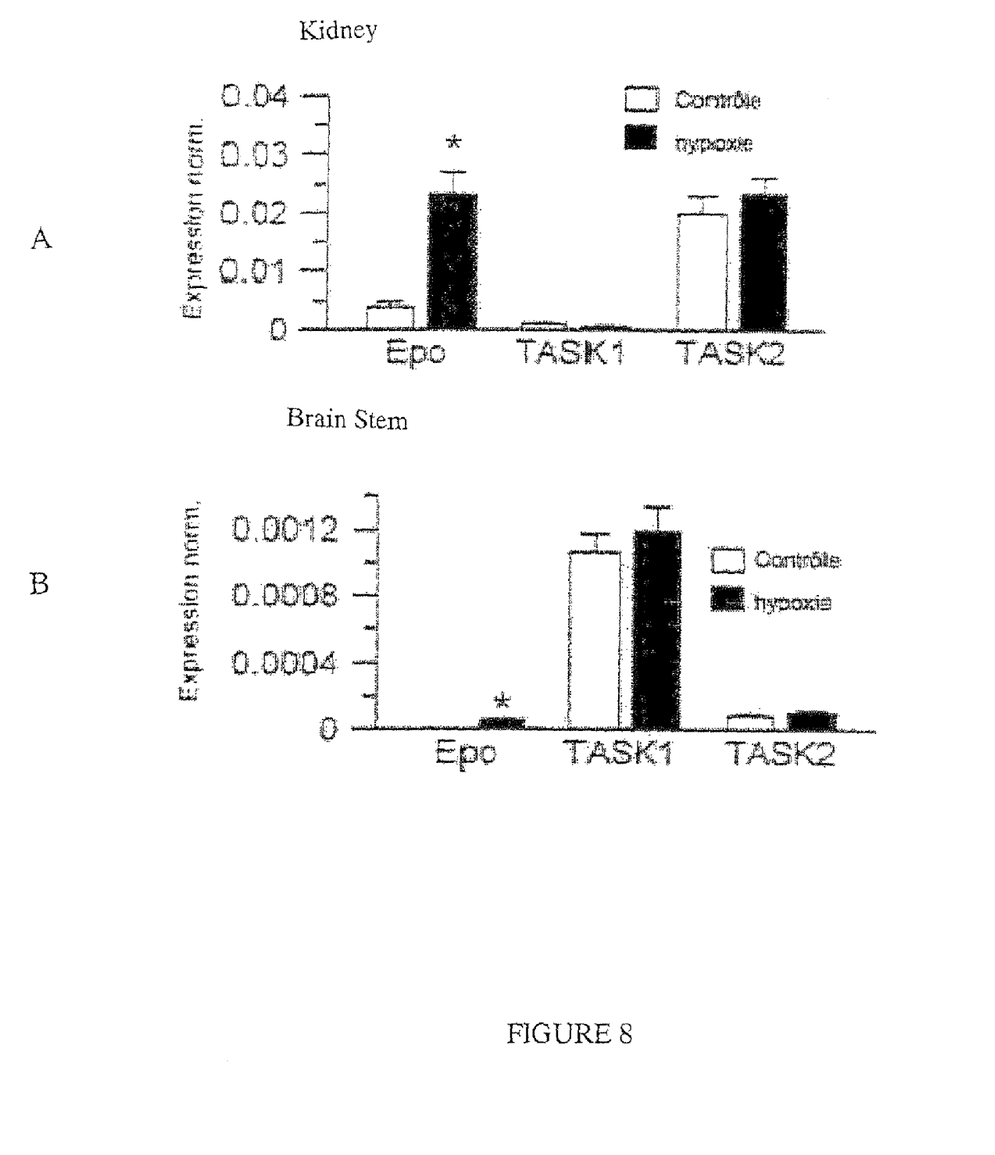
FIGS. 8A and 8B are histograms representing the expression of messenger RNA of TASK-1, TASK-2 and erythropoietin (EPO) in the kidney and in the brain stem in mice kept for 12 hours in a hypoxic environment. It consists of quantitative PCR results (8 mice per group).

During the first three to four hours of hypoxia, the control mice demonstrated a high depression in the respiratory flow with a prolongation in the time of expiration and a reduction in the respiratory frequency. This phase was followed by an adaptation phase characterised by a reduction in the time of expiration that returned to normal values after 10 to 12 hours (FIGS. 8B and C).

During the entire period of hypoxia, the respiratory parameters did not change in the TASK-2$^{-/-}$ mouse. Therefore, these mice presented a respiratory phenotype similar to that of the control mice after adaptation.

Moreover, the expression of TASK-2 was measured.

The mice were placed in an environment with 10% oxygen for 24 hours and the expression of the RNA messengers of TASK-2 (as well as TASK-1 and erythropoietin in controls) was then measured.

The RNA was isolated from the kidney and the brain stem of the mice using the Mini RNeasy Kit (Qiagen). For the reverse transcription, a reverse transcriptase (Promega) was used according to the protocol provided by the manufacturer. A chain polymerisation reaction in real time was carried out with the LightCycler system (Roche) using the PCR SYBR Green Kit (Qiagen). The transcription of the TASK-2, TASK-1 genes and erythropoietin was measured and standardised with respect to the expression of beta-actine.

The primers used and the conditions to carry out the chain polymerisation reaction in real time were as follows. Primers for beta-actin: sense primer, 5' CCACCGATCCACACA-GAGTACTT 3' (SEQ ID No. 1); antisense primer, GACAG-GATGCAGAAGGAGATTACTG 3' (SEQ ID No. 2). Primers for erythropoietin: sense primer, 5' AGAATGGAGGTG-GAAGAACAG 3' (SEQ ID No. 3); antisense primer, 5' TGTCTATATGAAGCTGAAGGGT 3' (SEQ ID No. 4). Primers for TASK-2: sense primer, 5' GCTTTGGG-GACTTTGTGG 3' (SEQ ID No. 5); antisense primer, 5' AAAGAGGGACAGCCAAGC 3' (SEQ ID No. 6).

The temperature for the hybridation of the primers was 55° C.

The results demonstrated that the quantity of RNAm coding for TASK-2 does not change in the kidney and in the brain stem during hypoxia. (FIGS. 8A and B).

The transcription of the TASK-2 gene therefore does not change during prolonged hypoxia. Therefore, the TASK-2 potassium channel is a new target to inhibit respiratory depression and stimulate respiration in conditions of hypoxia. As demonstrated before, the inactivation of TASK-2 is therefore a new strategy that differs from the therapeutic approaches used in prior art.

Example 7

In Vitro Demonstration of the Intervention of TASK-2 Channels in the Mechanisms of the Central Adaptation of Respiration This experiment was carried out in conditions and on mice identical to those used in example 2.

This experiment demonstrates the changes in the respiratory activity during anoxia, acidosis and alkalosis.

Figure 9:
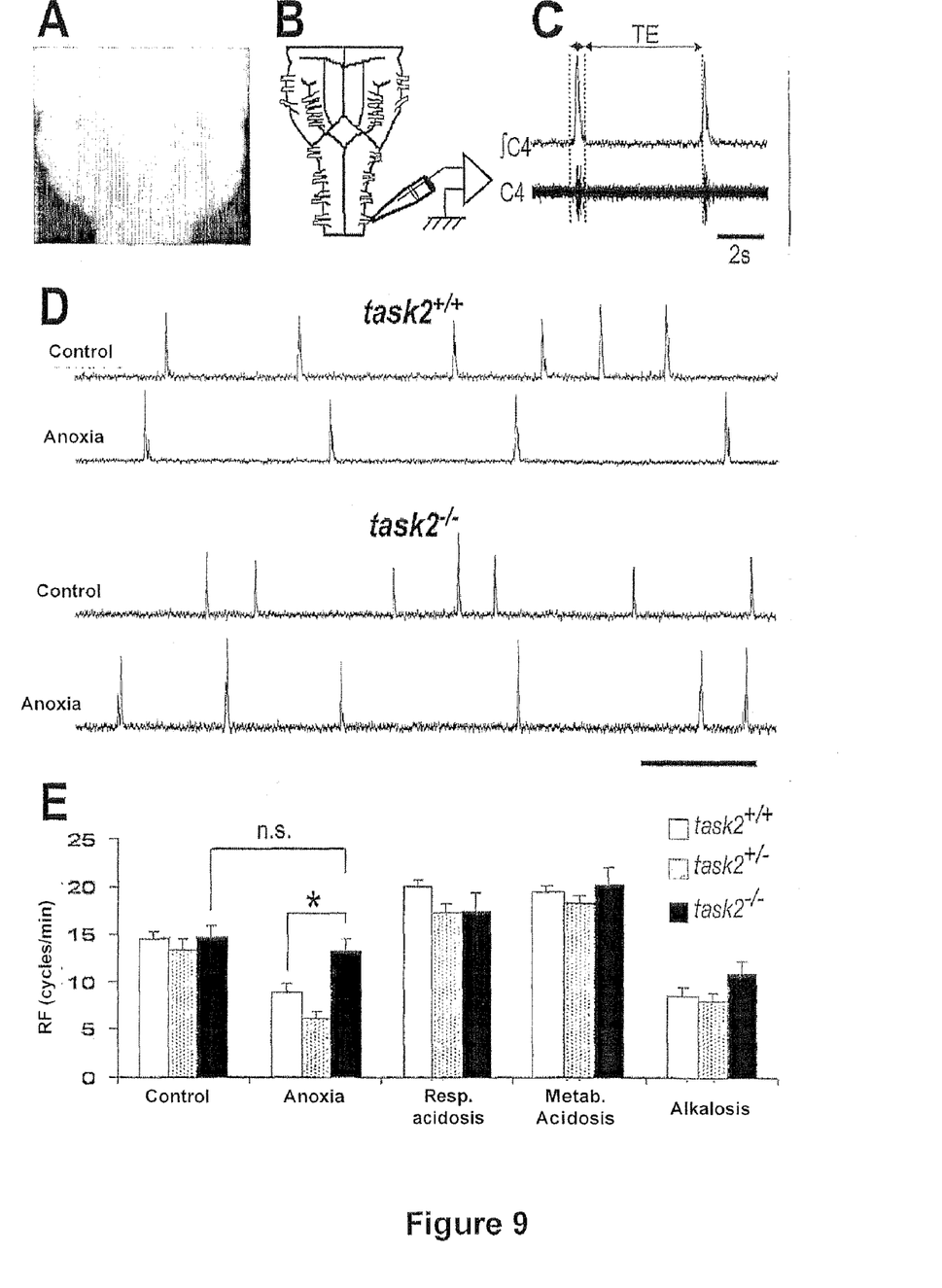
FIG. 9A illustrates the expression of TASK-2 in the zone located around the facial motor nucleus (retrotrapezoid nucleus and parafacial respiratory group) and on the whole brain in the 1 day old mouse. This zone is conserved in the "en bloc" registration technique.
FIG. 9B: diagram of the "en bloc" preparation where the structures of the spinal bulb and the most caudal part of the pons are conserved. An electrode placed on cervical root C4 can be used to record the activity of the phrenic nerve representing the respiratory activity.
FIG. 9C: example of the coding (C4) and integration (∫C4) of the inspiration burst used to measure the amplitude, surface and duration of the phases of inspiration (TI) and expiration (TE).
FIG. 9D: examples of respiratory activity. (∫C4) in normoxic (control) and anoxic conditions obtained on "en block" preparation of wild type (task 2+/+) or mutant task 2−/−) mice.
FIG. 9E: Histogram of the respiratory frequencies (RF) in control conditions, anoxia, respiratory or metabolic acidosis and alcalosis for wild type (NT), heterozygote (task 2+/−) mice.

An "en bloc" preparation of brain stems from neonatal mice that included the central chemoreceptors was carried out (FIG. 9A-C).

The "en bloc" preparation was carried out on 1 to 3 day old mice. Each mouse was anaesthetised with halothane, The brain stem and the cervical spinal cord were isolated and transferred in a recording chamber, the ventral part turned up, and perfused with an artificial cerebrospinal fluid at a rate of 4 ml·min$^{-1}$.

The respiratory frequency, duration of the inspiration bursts, the amplitude and surface area of the breaths was measured.

Ten TASK-2$^{+/+}$ mice, 8 TASK-2$^{+/-}$ mice and 7 TASK-2$^{-/-}$ mice were used in this experiment.

The basic respiratory frequency was identical in all individuals in normal conditions. In the control mice, a metabolic or respiratory acidosis induced an increase in the respiratory frequency (about +40%), while alkalosis and anoxia provoked a significant decrease in the respiratory frequency (about −40%).

The TASK-2−/− mice demonstrated reductions in the respiratory frequency similar to the change in pH. However, this response to the anoxia was completely eliminated in the TASK-2−/− mice (FIGS. 9D and E).

In the TASK-2−/− mouse, this experiment shows that there is a response to the hypoxia, expressed by an increase in the duration of the inspirations without a change in the respiratory frequency.

Therefore, the TASK-2 potassium channel is therefore a new target to inhibit the respiratory depression and stimulate the respiration in conditions of hypoxia.

Example 8

Application of Screening According to the Present Invention

The distribution of TASK-2 in an adult human being, its chromosome map, its biophysical and pharmacological properties and its regulation by the external pH were studied according to document WO 00/27871.

The following screening is used. HEK cells (Human Embryonic Kidney cells) are transfected with a plasmid containing complementary DNA from the gene of the human TASK-2 channel (pIRES-CD8-hTASK2) by the lipofectamine method. After 24 hours of culture, the TASK-2 currents are recorded using the voltage-clamp method (patch-clamp in whole cell configuration). The currents are activated by jumps in voltage from a rest potential at −95V to variable values ranging from −80 to +45 mV.

The currents are recorded in whole cell configuration using an EPC-10 amplifier (HEKA). The <<patch>> pipette contains a solution of 95 K-gluconate, 30 mM KCl, 4.8 mM $Na_2HPO_4$, 1.2 mM $NaH_2PO_4$, 5 mM glucose, 2.38 mM $MgCl_2$, 0.726 mM $CaCl_2$, 1 mM EGTA, 3 mM ATP, pH 7.2. The external solution is a RINGER solution: 145 mM NaCl, 0.4 mM $KH_2PO_4$, 1.6 mM $K_2HPO_4$, 5 mM glucose, 1 mM $MgCl_2$, 1.3 mM $CaCl_2$, 5 mM HEPES, pH 7.4.

Different drugs may be applied at different concentrations by perfusion of the external bath and their effects are evaluated by the change in the currents compared with the control conditions.

Figure 4:
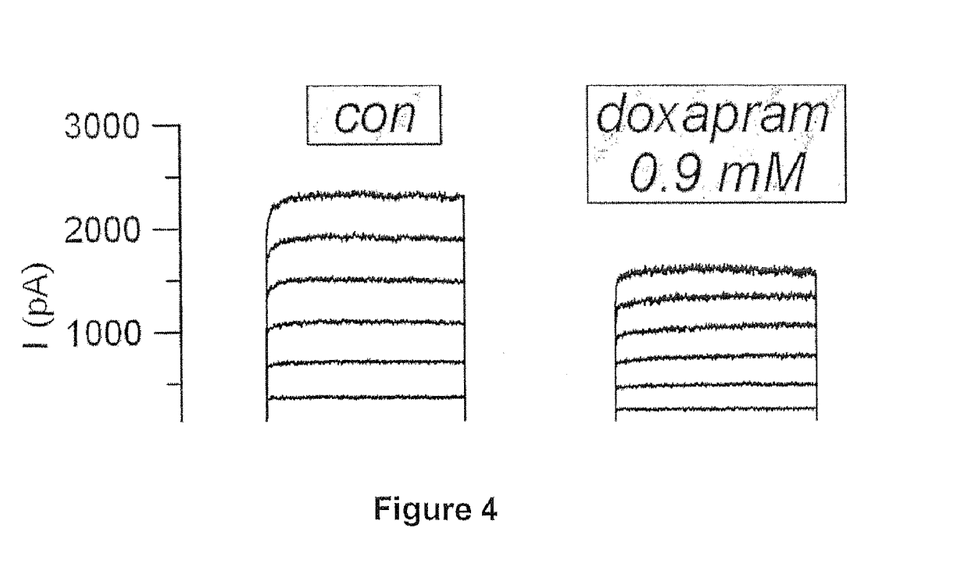
FIG. 4 represents a <<patch-clamp>> recording of the TASK-2 current (intensity I in picoamperes (pA)) on HEK cells transfected with DNA coding for the human TASK-2 channel.
Figure 5:
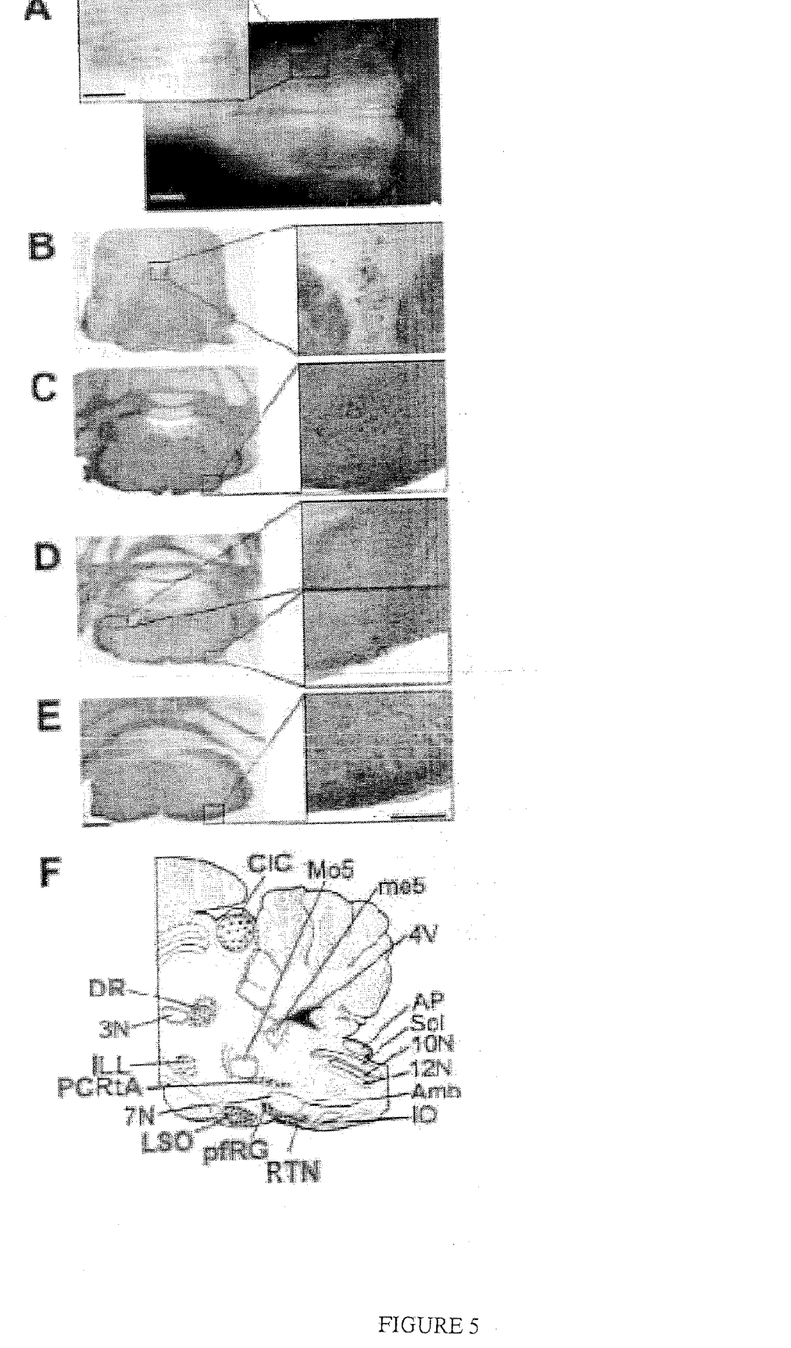

In the example in FIG. 4, the application of Doxapram at 0.9 mM in the batch is shown to reduce the current by 25% as attested by the jumps in potential.

The invention claimed is:

1. A screening method for identifying candidate molecules that might be used for the treatment of respiratory conditions in humans due to a dysfunction in the central nervous system, wherein said screening method comprises a first in vitro step which determines whether the functional activity of a TASK-2 polypeptide in the presence of a test molecule is decreased or eliminated compared with the functional activity of said TASK-2 polypeptide in the absence of said test molecule, and a second in vivo step, wherein a test molecule that decreases or eliminates said functional activity in the first in vitro step is administered to non-human animal model presenting a respiratory disorder, wherein a molecule that reduces the presentation of the respiratory disorder in the animal model is a candidate molecule for the treatment of respiratory conditions in humans due to a dysfunction in the central nervous system.

2. The method of claim 1, in which the step to determine whether the functional activity of a TASK-2 polypeptide is decreased or eliminated comprises:

i) contacting a cell expressing a TASK-2 polypeptide presenting a functional activity, with said test molecule, and ii) measuring the functional activity of the TASK-2 polypeptide.

3. The method of claim 2, wherein said cell expresses the TASK-2 polypeptide in an endogenous manner.

4. The method of claim 2, wherein said cell expresses the TASK-2 polypeptide in recombinant form.

5. The method of any one of claims 1 to 4, wherein said functional activity is determined by a measurement selected from the group comprising: measuring the ion current crossing the TASK-2 polypeptide, measuring the change in the membrane potential of the cell expressing the TASK-2 polypeptide, and measuring the change in intracellular ion concentration of the cell expressing the TASK-2 polypeptide.

6. The method of claim 5, wherein said functional activity is determined measuring the ion current crossing the TASK-2 polypeptide, and wherein the ion current crossing the TASK-2 polypeptide is an efflux of rubidium ions.

* * * * *

```
                          SEQUENCE LISTING

<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccaccgatcc acacagagta ctt                                             23

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gacaggatgc agaaggagat tactg                                           25

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agaatggagg tggaagaaca g                                               21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tgtctatatg aagctgaagg gt                                              22

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
```

-continued

```
           oligonucleotide

<400> SEQUENCE: 5
gctttgggga ctttgtgg                                                       18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
           oligonucleotide

<400> SEQUENCE: 6
aaagagggac agccaagc                                                       18
```